(12) United States Patent
Åkerfeldt et al.

(10) Patent No.: US 7,938,846 B2
(45) Date of Patent: May 10, 2011

(54) FEMORAL COMPRESSION DEVICE

(75) Inventors: Dan Åkerfeldt, Uppsala (SE); Leif Smith, Uppsala (SE); Marie Lindström, Grillby (SE); Tobias Adenmark, Uppsala (SE)

(73) Assignee: Radi Medical Systems AB, Uppsala (SE)

( * ) Notice: Subject to any disclaimer, the term of this patent is extended or adjusted under 35 U.S.C. 154(b) by 991 days.

(21) Appl. No.: 11/767,179

(22) Filed: Jun. 22, 2007

(65) Prior Publication Data
US 2008/0319328 A1    Dec. 25, 2008

(51) Int. Cl.
*A61B 17/00* (2006.01)
(52) U.S. Cl. ........................................ 606/201
(58) Field of Classification Search ............... 600/494, 600/498, 490, 499, 493; 606/201; 251/90, 251/92, 93, 95; 200/61.86
See application file for complete search history.

(56) References Cited

U.S. PATENT DOCUMENTS

| | | | | |
|---|---|---|---|---|
| 592,279 | A * | 10/1897 | Conihe | 251/95 |
| 3,254,671 | A * | 6/1966 | Berliner | 137/565.12 |
| 4,037,587 | A * | 7/1977 | Kaneda et al. | 600/498 |
| 4,072,171 | A * | 2/1978 | Nakazawa | 137/599.18 |
| 4,200,259 | A * | 4/1980 | Ueda | 251/285 |
| 4,282,881 | A * | 8/1981 | Todd et al. | 600/487 |
| 4,290,434 | A * | 9/1981 | Jewett | 600/493 |
| 4,294,261 | A * | 10/1981 | Baker et al. | 600/504 |
| 4,416,287 | A * | 11/1983 | Riester | 600/498 |
| 4,747,412 | A * | 5/1988 | Yamaguchi | 600/496 |
| 4,796,184 | A * | 1/1989 | Bahr et al. | 600/492 |
| 4,962,764 | A * | 10/1990 | Matsumura | 600/504 |
| 5,307,811 | A * | 5/1994 | Sigwart et al. | 600/490 |
| 5,542,427 | A * | 8/1996 | Åkerfeldt | 600/490 |
| 5,645,563 | A | 7/1997 | Hahn et al. | |
| 5,944,054 | A * | 8/1999 | Saieva | 137/625.4 |
| 7,468,038 | B2 * | 12/2008 | Ye et al. | 600/490 |

(Continued)

FOREIGN PATENT DOCUMENTS

EP    0 462 088 A2    12/1991

(Continued)

OTHER PUBLICATIONS

Kingyield Instruction Manual for Semi-Automatic Mini Style Digital Blood Pressure Monitor, Model No. BP101U, Kingyield Hongkong Limited, 9 pgs., Mar. 23, 2007.

*Primary Examiner* — Todd E Manahan
*Assistant Examiner* — Erin Colello
(74) *Attorney, Agent, or Firm* — Foley & Lardner LLP

(57) ABSTRACT

A femoral compression device (1) for compressive bearing against the femoral artery of a patient, comprising a base plate (2), an inflatable air cushion (4), and an electronic manometer (8) connected to the inflatable air cushion for measurement of the current pressure difference between the pressure prevailing inside the inflatable air cushion and the ambient air pressure. The femoral compression device can further comprise a mechanical device (11; 46) which prevents an air opening leading to the inflatable air cushion from being closed before the manometer is zeroed. In another embodiment, an electronic manometer is provided such that a current characteristic of an electric signal representing the current pressure difference can be compared with a corresponding characteristic which was obtained at zero pressure difference and which was stored in the electronic manometer, wherein the manometer cannot be zeroed as long as the current characteristic deviates more than a predetermined amount from the stored characteristic.

17 Claims, 3 Drawing Sheets

U.S. PATENT DOCUMENTS

| | | |
|---|---|---|
| 2003/0139766 A1 | 7/2003 | McEwen et al. |
| 2004/0122469 A1* | 6/2004 | Akerfeldt et al. .............. 606/201 |
| 2004/0176796 A1* | 9/2004 | Akerfeldt et al. .............. 606/201 |
| 2007/0142731 A1* | 6/2007 | Ye et al. ......................... 600/494 |
| 2008/0097475 A1* | 4/2008 | Jaggi et al. .................... 606/130 |

FOREIGN PATENT DOCUMENTS

| | | |
|---|---|---|
| GB | 2 085 198 A | 4/1982 |
| WO | WO 2007/016765 A | 2/2007 |

* cited by examiner

FEMORAL COMPRESSION DEVICE

FIELD OF THE INVENTION

The invention relates generally to a femoral compression device, and in particular to a femoral compression device comprising an electronic pressure gauge.

BACKGROUND OF THE INVENTION

Femoral compression devices for applying pressure on a patient's femoral artery after completion of an interventional procedure are known. An example of such a femoral compression device is disclosed in the patents U.S. Pat. No. 5,307,811 and EP 0 462 088, which are assigned to the present assignee. The entire contents of these documents are incorporated herein by reference for the devices, methods, and techniques disclosed therein.

A femoral compression device according to these publications comprises basically a pressurizing means for compressive bearing against a puncture site at a femoral artery of a patient, a belt adapted to be fixed around the patient's body, and a base plate supporting the pressurizing means and being provided with two extensions. In use, the pressurizing means, which in one embodiment has the form of an inflatable semi-spherical air cushion, is positioned over the femoral artery, and the belt, which extends from the end of the first extension, around the patient's body and to the end of the second extension, is tightened. To apply pressure on the femoral artery, the inflatable semi-spherical air cushion is inflated by a pump to a certain predetermined pressure, which is read from a pressure gauge.

SUMMARY OF THE INVENTION

In a femoral compression device of the aforementioned type, the flow of blood through the femoral artery of a patient is ideally stopped when the air cushion has been inflated to a pressure equal to the systolic pressure prevailing in the femoral artery. Due to pressure loss to surrounding tissue, the corresponding protocol for pressure management prescribes however that the air cushion is inflated to a pressure which is about 10 mmHg to 20 mmHg above the patient's systolic pressure, which before the start of the compression procedure has been measured by other well-known means.

In the known femoral compression device, the pressure gauge comprises a mechanical manometer with an analog pointer. It can therefore be appreciated that the pressure measurement system is rather insensitive, i.e. small pressure changes will not be registered by the analog pointer due to friction and the inherent inertia of the mechanical components of the manometer. This means, for example, that the manometer is not capable of indicating when the blood flow through a femoral artery has been cut off, something which ideally should be possible to note by observing the discontinuation of small regular pressure variations inside the air cushion, the pressure variations being induced by the systolic pulses in the femoral artery over which the air cushion has been positioned. By observing the ceasing of systolic pulses, the pressure applied to the femoral artery could be fine-tuned to the medical condition of the patient who is undergoing the medical treatment in question, i.e. application of an excessive amount of pressure could be avoided, which spares the patient from discomfort and expedites the time of treatment.

Pressure gauges, which are based on electronics rather than on mechanics, are known in other medical applications. For example, the company Kingyield Hong Kong Limited manufactures several different models of digital blood pressure monitors, which include a pump, an inflatable cuff, and an electronic manometer with a digital display. In use, the inflatable cuff is placed around a patient's upper arm, the cuff is inflated by the pump to a pressure above the expected systolic pressure, and while air is slowly leaking out of the cuff the systolic and diastolic pressures are measured by the manometer and displayed on the digital display. As is normal in the art, these blood pressure monitors are not sealed air-tight systems but slowly leaking systems, and are as such completely unsuited for the present application, as will be understood from the description below.

Consequently, there is still a need for an improved femoral compression device comprising a pressure gauge which obviates the drawbacks associated with femoral compression devices according to the prior art.

Embodiments of the invention are directed to a femoral compression device with an inflatable air cushion and a pressure gauge in the form of an electronic manometer comprising an electronic circuit with at least one pressure-sensitive element and a digital display for displaying the pressure prevailing inside the inflated air cushion.

An electronic manometer does further provide for possibilities regarding how the measured pressure is displayed for a user. The output pressure values can, for example, be averaged values over a certain time interval to filter out artefacts induced by the patient's movements, i.e. a damping can easily be incorporated in the system.

Further embodiments of the invention are directed to a femoral compression device comprising an electronic manometer provided with a mechanical actuator that prevents the manometer from being zeroed when a pressure above the ambient air pressure is prevalent in an inflatable air cushion. In another embodiment the same effect is achieved by comparing a pre-stored original value of a pressure signal with a corresponding actual value, and only allowing zeroing of the electronic manometer if these two values are essentially equal.

DETAILED DESCRIPTION OF PREFERRED EMBODIMENTS

Figure 1:
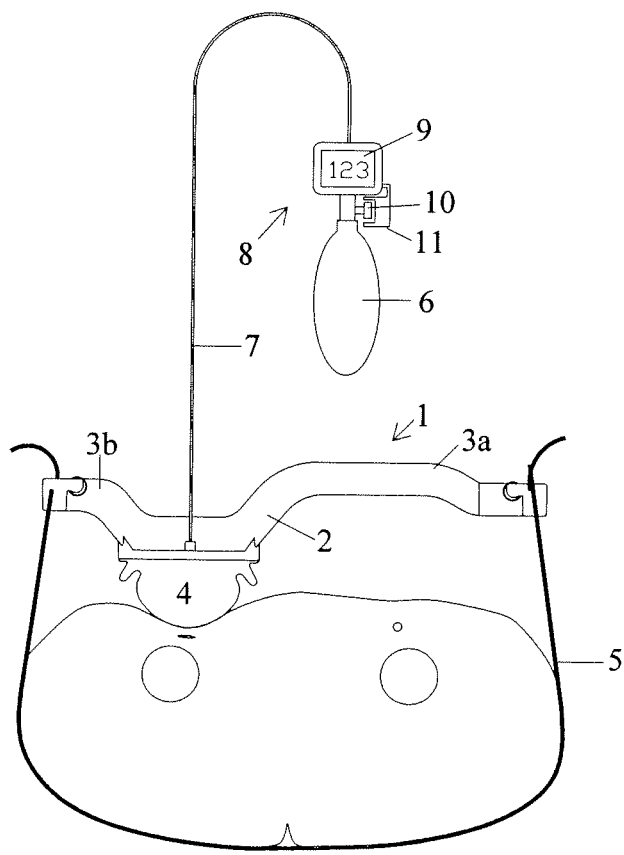
FIG. 1 illustrates schematically a femoral compression device with an electronic manometer according to one embodiment of the present invention.

In FIG. 1, a femoral compression device 1 is schematically illustrated. The femoral compression device 1 comprises a base plate 2 with two extensions 3a and 3b, an inflatable air cushion 4, a belt 5, a pump 6, an air connection 7, and an electronic pressure gauge or manometer 8 with a display 9. Except for the manometer 8 and possibly the pump 6, the femoral compression device 1 is of the same construction as was disclosed in the previously mentioned patents U.S. Pat.

No. 5,307,811 and EP 0 462 088. In use, the inflatable and semi-spherical air cushion 4 is positioned over the femoral artery of a patient, and the belt 5, which extends from the end of the first extension 3a, around the patient's body and to the end of the second extension 3b, is tightened and secured by belt fasteners at the end of each extension. To apply pressure on the femoral artery, the inflatable semi-spherical air cushion 4 is inflated by the pump 6 to a certain pressure, which is measured by the manometer 8 and displayed on the display 9. The manometer 8 comprises further a vent knob 10, which is covered by a cap 11. The functions of the vent knob 10 and in particular the cap 11 will be discussed in detail below.

Figure 2:
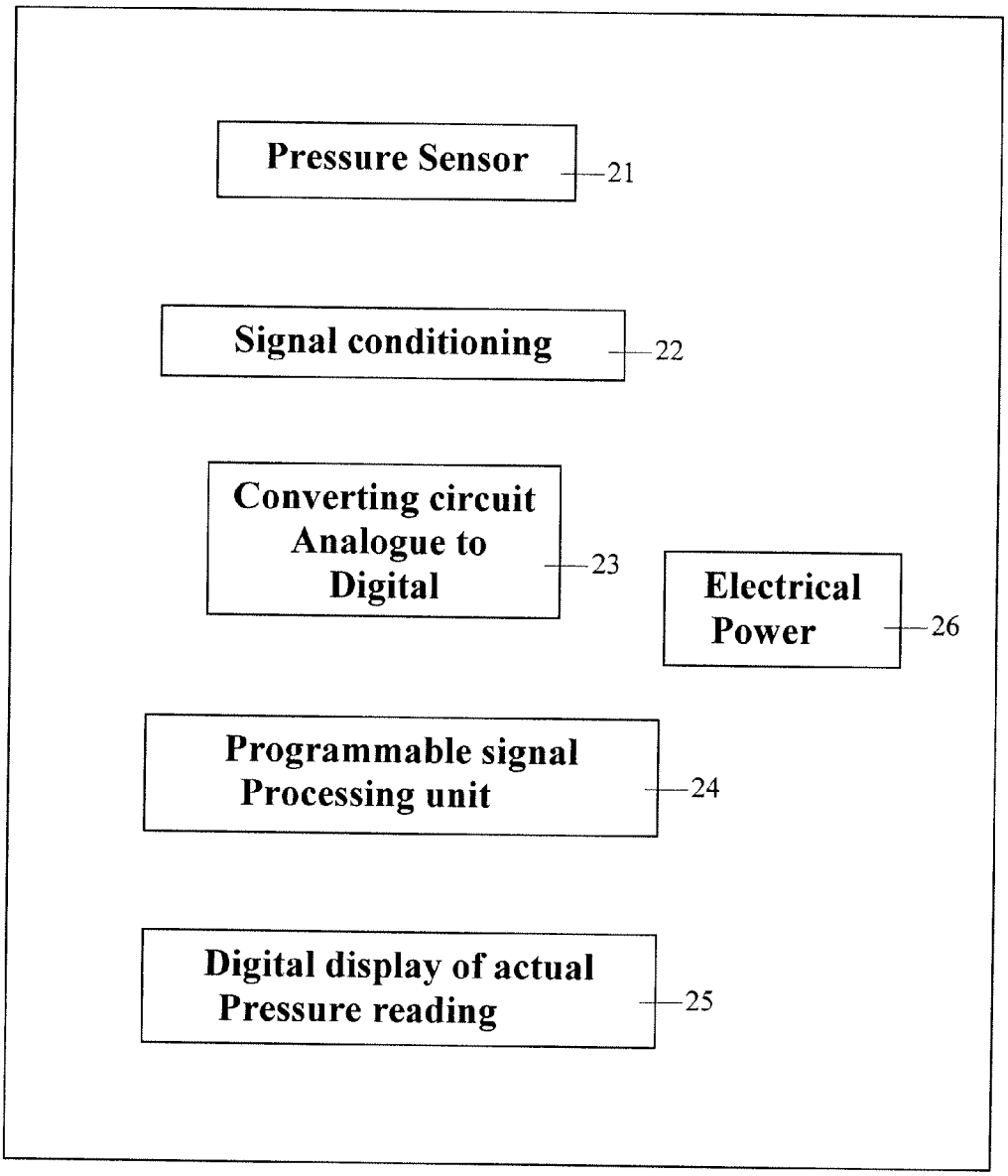
FIG. 2 represents an exemplifying block diagram for the manometer of FIG. 1.

FIG. 2 represents a block diagram for an electronic manometer according to one embodiment of the present invention. As the person skilled in the art readily will appreciate, the diagram is only an illustrative example of one embodiment of the manometer, and several of the blocks in FIG. 2 could be integrated into one electronic circuit, or even completely omitted, depending on the functionally of other circuits and components in the electronic manometer as well as depending on user preferences. More specifically, FIG. 2 illustrates that an electronic manometer can comprise a pressure sensor 21, signal conditioning circuits 22, converting circuits 23, a programmable processing unit 24, and a digital display 25, which all, if necessary, are powered by a power supply 26. The pressure sensor 21 can be of different constructions, but generally it is a device that converts a physical pressure into an electrical quantity, wherein the magnitude, or some other characteristic, of the electrical quantity depends on the magnitude of the pressure applied. A capacitive pressure sensor is discussed below in conjunction with FIG. 3. The output from the pressure sensor 21 is provided to the signal conditioning circuit 22, which processes the output from the pressure sensor 21 in a suitable manner. The signal conditioning process can, for example, comprise amplification, filtering, differentiation, integration and/or averaging, as required by the functionality of the pressure sensor 21 and the other components of the manometer. In this example, the output signal from the signal conditioning circuit 22 is then directed to a signal converting circuit 23, which comprises an analog-to-digital converter for converting the analog signals to binary numbers. In the programmable processing unit 24 these binary numbers are then transformed to pressure values by comparing the binary numbers with calibration data stored in the programmable processing unit 24. The pressure values are finally presented on the digital display 25. In this particular embodiment, display 25 is the same component as display 9 of FIG. 1 and the components of FIG. 2 are part of manometer 8 of FIG. 1. Components of the electrical manometer that need electrical power are preferably powered by the common power supply 26, e.g., in the form of a battery. It is also possible that certain parts, such as the digital display, are separately powered by another power supply.

Figure 3:
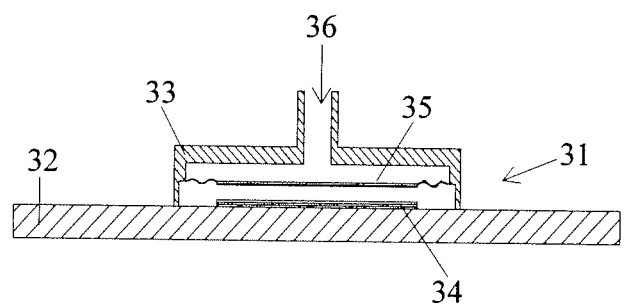
FIG. 3 shows an example of a pressure sensitive device which is part of the manometer of FIG. 1.

An example of a pressure sensor 31, suitable for use as pressure sensor 21, is schematically illustrated in FIG. 3. This pressure sensor 31 is a capacitive sensor comprising a support plate 32 provided with a housing 33 having a conductive bottom surface 34 and an air inlet 36. Inside the housing 33 and resiliently attached to the inner walls of the housing 33, a conductive plate 35 is suspended such that the underside of the conductive plate 35 is essentially parallel with the conductive bottom surface 34. When an electrical voltage is applied over the bottom surface 34 and the conductive plate 35, a capacitor is formed, the capacitance of which depends on the distance between the conductive plate 35 and the bottom surface 34. When the conductive plate 35 experiences an increased physical pressure, originating from e.g. the air pressure prevailing inside an inflatable air cushion like inflatable air cushion 4 of FIG. 1 and having access to the housing 33 via the air inlet 36, the conductive plate 35 will move downwards and towards the bottom surface 34, which changes the distance between the bottom surface 34 and the conductive plate 35 and thereby changes the capacitance of the pressure sensor 31. In the same way, if the pressure on the conductive plate 35 is reduced, the conductive plate 35 will move away from the conductive bottom surface 34. The output from the pressure sensor 31 will therefore be dependent on the applied pressure, and the output signal can be applied to a signal conditioning circuit, as was described above in conjunction with FIG. 2. Many other types of pressure sensors based on different physical principles, such as piezoresistivity, can be utilized in an electronic manometer according to the present invention.

As was briefly mentioned above, electronic manometers are known in medical applications comprising blood pressure monitoring. A blood pressure monitoring system comprising an inflatable cuff, a pump, and an electronic manometer is however, generally a leaking system, because in use the cuff is inflated to a pressure above the expected systolic pressure and while air is slowly leaking out of the cuff, the systolic and diastolic pressures are measured. The inventors believe that a pump and an electronic manometer designed for blood pressure monitoring can therefore not be used in the present application, because here it is necessary that an inflatable air cushion is capable of maintaining the same pressure over an extended period of time.

Further, in the present application it should be clear that the pressure gauge is showing the pressure difference between the pressure prevailing inside an inflatable air cushion and the ambient air pressure. In a femoral compression device with a mechanical manometer, the pressure reacting components, which typically incorporate a mechanical spring, are tuned such that the manometer shows zero pressure when the ambient air pressure is equal to the pressure inside the air cushion, e.g. when the air cushion is vented. Conversely, if the air cushion is inflated and not subsequently vented, a mechanical manometer will show a pressure different from zero. For an electronic manometer the situation is quite different. Usually, an electronic manometer can be zeroed at an arbitrary time, i.e. at an arbitrary pressure; and an electronic manometer is often automatically zeroed when it is turned on. In a blood pressure measuring application this is not satisfactory as it would imply that the blood pressure finally measured would depend on whether or not the inflatable component, e.g. an inflatable cuff, was already inflated at the time the electronic manometer was zeroed. However, as blood pressure monitors usually are leaking systems this is not a real problem since any air accidentally pumped into the cuff will leak out, and the manometer is usually zeroed at zero pressure difference. To further prevent that the blood pressure monitor is zeroed when there still is some excess pressure in the cuff, the manometer can be provided with an electronic circuit which compares the pressure prevailing inside the cuff over time, and prevents that the manometer is zeroed as long as the magnitude of this pressure drops.

Also in the compression device according to embodiments of the present invention it is not acceptable that an electronic manometer is zeroed when air has already been inflated into an inflatable air cushion, because that would lead to an excessive amount of pressure being applied to the puncture site over which the air cushion has been positioned, when the corresponding pressure managing protocol is followed by a user. For example, if the protocol prescribes that the air cushion should be inflated to a pressure of 15 mmHg above the systolic pressure, and the systolic pressure has been measured to be 130 mmHg, the air cushion should be inflated to a pressure of 145 mmHg. If, however, the manometer is turned on and zeroed when some air, in this example representing an overpressure of 10 mmHg, already has been pumped into the air cushion, the applied pressure would in reality amount to 155 mmHg, which is wrong. Further, this problem cannot be solved by a solution based on comparison of pressure readings over time, because the present system is a sealed system, and it cannot for all situations be assumed that the air cushion is properly vented before the electronic manometer is turned on and zeroed.

Returning now to FIG. 1, wherein the vent knob 10 and its cap 11 are illustrated. The cap 11 is connected to a non-conducting strip (not illustrated in FIG. 1), which has been placed between the poles of a battery and the adjacent battery connectors, such that the battery is prevented from powering the electronic circuits of the manometer 8. By removing the cap 11 and its appended strip, a user initiates the manometer 8, i.e. the electronic circuits of the manometer 8 are powered and at the same time the manometer 8 is zeroed. The latter action is justified by the fact that before the femoral compression device 1 leaves the manufacturing site, the vent knob 10 has been placed in an open position that corresponds to a vented system, i.e. the air cushion 4 is in open communication with the ambient air. With the vent knob 10 being left in this open position, the cap 11 is placed over the vent knob 10, to ensure that the vent knob 10 is not tampered with before use of the femoral compression device 1. By this measure it is ensured that the manometer 8 is zeroed when the pressure difference between the ambient air pressure and the pressure prevailing inside the air cushion 4 actually is zero. When the manometer 8 has been zeroed, the vent knob 10 is turned to a position corresponding to a closed system, and the inflatable air cushion 4 is inflated by means of the pump 6.

From the above it should be clear that the skilled person could envisage several different solutions based on the principle that a femoral compression device is delivered with a vented air cushion and an electronic manometer, the zeroing of which can only occur after the removal or manipulation of a mechanical member or actuator, which, before it is removed or manipulated, prevents the air cushion from being put in a state wherein it is not in open communication with the ambient air pressure. Preferably the femoral compression device is a single-use device and the mechanical arrangement for preventing zeroing at an actual pressure difference being different from zero is most easily provided at the time when the femoral compression device is manufactured. Alternatively, parts of a femoral compression device, such as an inflatable air cushion with an integrated manometer, can be single-use devices provided with the mechanical device discussed above, while a base plate with extensions are designed for multiple uses. For a single-use device, regardless whether it is only an inflatable air cushion attachable to a multi-use device or a complete single-use device, a corresponding electronic manometer can advantageously be designed such that the manometer ceases to function (i.e. no values are presented on a display) after a certain preset time period, e.g., 24, 48 or 72 hours, after the manometer was turned on, to prevent that the manometer and the corresponding femoral compression device are used several times. A reason for such a measure is, among other reasons, that a power source, e.g. a battery, can only power an electronic manometer for a finite period of time; and when this time period has expired correct measurements can no longer be guaranteed although the manometer may give a user the impression that the manometer works properly, which is a situation that is highly unwanted. The irrevocable and automatic shutdown of an electronic manometer can be accomplished by suitably designed hardware, i.e. some electric circuits could melt such that, e.g., a short circuit is created, after a preset time, or an electronic manometer could be caused to shut down after a preset time by suitable software programming.

Figure 4A:
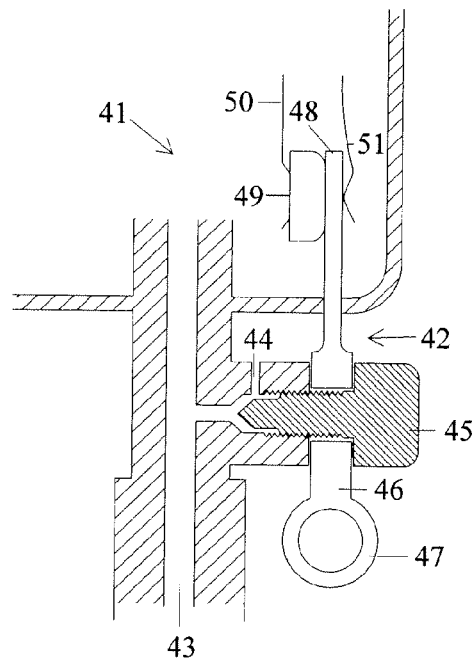
FIGS. 4a and 4b illustrate a mechanical arrangement for ensuring that a manometer is turned on and zeroed when an air cushion is vented.
Figure 4B:
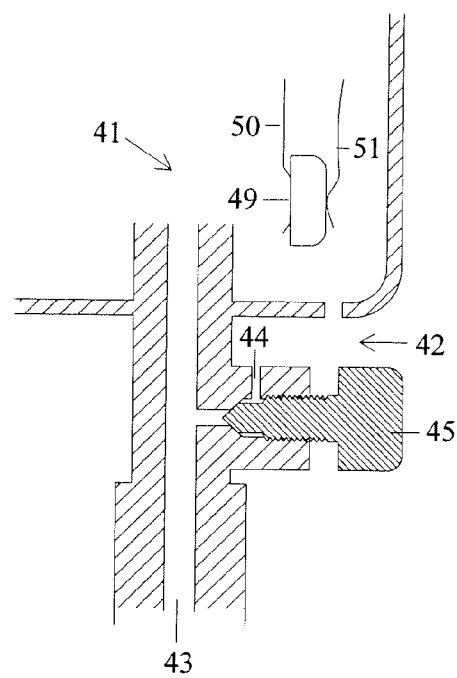

A femoral compression device can comprise many different kinds of mechanical devices which prevent an air opening leading to an inflatable air cushion from being closed before an electronic manometer is zeroed; and in FIGS. 4a and 4b another mechanical arrangement for assuring that an air cushion is in open communication with the ambient air is illustrated. More specifically, according to FIG. 4a and FIG. 4b, a manometer 41 comprises an air inlet system 42 having an air passage 43 with an air opening 44, a vent knob 45, a non-conductive safety pin 46 having a handle end 47 and an opposite securing end 48, battery 49, and a first fixed electrical connection 50 and a second springy electrical connection 51, which electrically connect the battery 49 to the other components of the manometer 41 (which are not shown in FIGS. 4a, b). The manometer 41 and its air inlet system 42 is delivered to a user in a configuration corresponding to FIG. 4a, which shows that the vent knob 45 is in such a position that air is free to flow into and out from the air passage 43 via the air opening 44. In this open position, the electrically non-conductive securing end 48 of the safety pin 46 is positioned between the battery 49 and the resilient electrical connection 51, such that the battery 49 cannot power the manometer 41. In other words, with the vent knob 45 in the open position of FIG. 4a, it is ensured that the pressure difference between the pressure prevailing inside an inflatable air cushion and the ambient air pressure is zero. In this particular embodiment, the open position of the vent knob 45 is accomplished by selecting the width of the safety pin 46 such that the vent knob 45 cannot be turned into a position wherein the air opening 44 is closed as long as the safety pin 46 is in place. In other embodiments (not shown in the Figures) the same effect can be achieved by positioning a safety pin in such a position that a vent actuator cannot be moved to a position wherein an air inlet opening is closed as long as the safety pin or some appended part thereof is in place.

When a user then wants to inflate an air cushion of a femoral compression device, he or she commences the procedure by removing the securing pin 46 by pulling on the handle end 47 of the securing pin 46. When the securing pin 46 with its securing end 48 has been removed, the springy second connection 51 comes into contact with the battery 49, which means that the electrical circuit is closed and the battery 49 can power the manometer 41. The manometer 41 is designed such that it is zeroed as soon as it is turned on, which—in accordance with the discussion in conjunction with FIG. 4a above—is done with the actual pressure difference being equal to zero. To inflate the air cushion, the vent knob 45 is turned to a position in which air opening 44 no longer is in open communication with air passage 43, and the air cushion can be inflated by means of a pump. The latter situation is illustrated in FIG. 4b.

Other measures are also possible when it comes to preventing an electronic manometer from being zeroed when the pressure difference between the pressure inside an inflatable air cushion and ambient air pressure is not equal to zero. In another embodiment of the present invention, when an electronic manometer is to be zeroed, the magnitude of an electric signal representing the current pressure difference between the pressure prevailing inside an air cushion and the ambient air pressure is compared with a corresponding value which, at the time of manufacture of a femoral compression device, was obtained at zero pressure difference and which was stored in, for example, a memory accommodated in a programmable processing unit which is part of the electronic manometer. More specifically, if the magnitude of the present electric signal is equal to the stored value, the electronic manometer is zeroed. On the other hand, if the magnitude of the present electric signal is not equal to the stored value, the electronic manometer can not be zeroed. To account for changes in the magnitude of an electric signal which are not due to an actual deviation from zero pressure, but arise from, for example, drift and ageing of the electronic components of the manometer, the criterion for allowing zeroing of the manometer is preferably that the magnitude of the signal is within an interval defined around the preset value.

Figure 5:
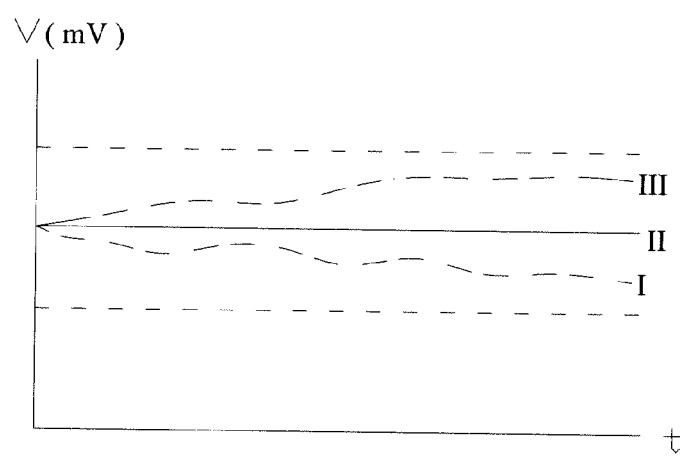
FIG. 5 is a diagram illustrating a possible temporal variation of an electrical signal corresponding to a pressure difference equal to zero in an electronic manometer according to the present invention.

In FIG. 5, the temporal appearance of the magnitude of a signal representing zero pressure difference is illustrated. FIG. 5 illustrates that the magnitude of a signal representing zero pressure difference can vary over time; and more particularly, the diagram of FIG. 5 shows three different possible behaviours: a first case (indicated with a dashed line and marked with I) wherein the magnitude (here measured in millivolt (mV)) of an electric signal drops with time t, a second case (indicated with a solid line and marked with II) wherein the magnitude remains unchanged, and a third case (indicated with a dashed line and marked with III) wherein the magnitude increases. It should now be appreciated that acceptance criteria can be set such that if, for example, a present signal has a magnitude of ±10% of the original signal amplitude, then the manometer in question could be zeroed, whereas if the present signal magnitude falls outside this interval of ±10%, then the manometer cannot be zeroed. In the latter case, the user should be advised to check whether the air cushion is properly vented such that no excess air has been trapped inside a closed air cushion. Here it should be noted that the term "magnitude" should not be taken too literally, because it is within the scope of the invention that other signal characteristics, such as an integrated value or an average value, could be used as a current value to be compared with a corresponding original value.

Although the present invention has been described with reference to specific embodiments, also shown in the appended drawings, it will be apparent for those skilled in the art that many variations and modifications can be done within the scope of the invention as described in the specification and defined with reference to the claims below.

What is claimed is:

1. A femoral compression device for compressive bearing against the femoral artery of a patient, comprising:
    a base plate;
    an inflatable air cushion attached to the base plate;
    a first extension extending from a first side of the base plate;
    a second extension extending from a second side of the base plate, said second side being opposite to the first side;
    a belt adapted to be attached to an end of the first extension and being adapted to extend around the patient's body to be attached to an end of the second extension;
    a pump connected to the inflatable air cushion for inflation of the inflatable air cushion;
    a manometer connected to the inflatable air cushion for measurement of a current pressure difference between pressure prevailing inside the inflatable air cushion and ambient air pressure, wherein the manometer is an electronic manometer; and
    a mechanical device comprising a closing portion, and a removable portion configured to prevent the manometer or circuits thereof from being electrically powered while preventing the closing portion from closing an air opening leading to the inflatable air cushion.

2. The femoral compression device according to claim 1, wherein the closing portion comprises a vent knob, by which the air opening leading to the inflatable air cushion can be closed or opened, wherein said vent knob at a time of manufacture of the femoral compression device is positioned such that the air opening is open, and wherein the removable portion is configured to prevent the vent knob from being maneuvered to a closed position before the manometer is zeroed.

3. The femoral compression device according to claim 2, wherein the removable portion comprises a removable cap, which is positioned over the vent knob and which is provided with a member that mechanically prevents the manometer from being zeroed by preventing the manometer or circuits thereof from being electrically powered as long as the removable cap has not been removed.

4. The femoral compression device according to claim 2, wherein the removable portion comprises a removable safety pin, which is positioned in engagement with the vent knob and which has a securing end portion that is configured to mechanically prevent the manometer from being zeroed by preventing the manometer, or circuits thereof, from being electrically powered as long as the removable safety pin has not been removed.

5. The femoral compression device according to claim 4, wherein the removable safety pin, as long as the removable safety pin is in place, is configured to ensure that the vent knob cannot be moved such that the air opening is closed.

6. The femoral compression device according to claim 1, wherein the electronic manometer is provided with electrical circuits such that a current characteristic of an electric signal representing the current pressure difference can be compared with a corresponding characteristic which, at a time of manufacture of the femoral compression device, was obtained at zero pressure difference and which was stored in a memory accommodated in said electrical circuits, and wherein the manometer cannot be zeroed as long as the current characteristic deviates more than a predetermined amount from the stored characteristic.

7. The femoral compression device according to claim 1, wherein the electronic manometer is configured to automatically shut down after expiration of a preset time period, which starts to run when the manometer is turned on for a first time.

8. The femoral compression device according to claim 1, further comprising a digital display configured to display the current pressure difference.

9. An inflatable air cushion assembly adapted for attachment to a femoral compression device, comprising:
    a manometer connected to an inflatable air cushion for measurement of a current pressure difference between pressure prevailing inside the inflatable air cushion and ambient air pressure, wherein the manometer is an electronic manometer; and
    a mechanical device comprising a closing portion, and a removable portion configured to prevent the manometer or circuits thereof from being electrically powered while preventing the closing portion from closing an air opening leading to the inflatable air cushion.

10. The inflatable air cushion assembly according to claim 9, wherein the closing portion comprises a vent knob, by which the air opening leading to the inflatable air cushion can be closed or opened, wherein said vent knob at a time of manufacture is positioned such that the air opening is open, and wherein the removable portion is configured to prevent the vent knob from being maneuvered to a closed position before the manometer is zeroed.

11. The inflatable air cushion assembly according to claim 9, further comprising an electrical circuit configured to zero the manometer when the manometer is powered up.

12. The inflatable air cushion assembly according to claim 9, wherein the removable portion comprises an interlock configured to ensure that the air cushion is vented when the manometer is zeroed.

13. The inflatable air cushion assembly according to claim 9, wherein the electronic manometer is configured to automatically shut down after expiration of a preset time period, which starts to run when the manometer is turned on for a first time.

14. The inflatable air cushion assembly according to claim 9, further comprising a digital display configured to display the current pressure difference.

15. A method of promoting healing of a blood vessel after completion of an interventional procedure which required access to a patient's vascular system via a puncture in the blood vessel, comprising:

removing a removable portion of a mechanical device configured to prevent an electronic manometer or circuits thereof from being electrically powered and to prevent a closing portion of the mechanical device from closing an air opening leading to an inflatable air cushion before being removed;

placing the inflatable air cushion in contact with the patient near the puncture; and monitoring air pressure inside the air cushion with the electronic manometer to determine a condition of the puncture.

16. The method according to claim 15, wherein the monitoring includes monitoring for presence or absence of periodic pressure variations induced by systolic pulses in the blood vessel.

17. The method according to claim 15, further comprising digitally displaying the air pressure inside the air cushion.

* * * * *